(12) United States Patent
Cherney

(10) Patent No.: US 10,234,368 B2
(45) Date of Patent: Mar. 19, 2019

(54) SYSTEM AND METHOD FOR LOAD EVALUATION

(71) Applicant: Deere & Company, Moline, IL (US)

(72) Inventor: Mark J. Cherney, Potosi, WI (US)

(73) Assignee: DEERE & COMPANY, Moline, IL (US)

( * ) Notice: Subject to any disclaimer, the term of this patent is extended or adjusted under 35 U.S.C. 154(b) by 212 days.

(21) Appl. No.: 15/293,048

(22) Filed: Oct. 13, 2016

(65) Prior Publication Data
US 2018/0106709 A1 Apr. 19, 2018

(51) Int. Cl.
| | | |
|---|---|---|
| G01G 7/00 | (2006.01) |
| G01G 9/00 | (2006.01) |
| G01G 11/00 | (2006.01) |
| G01G 19/14 | (2006.01) |
| G01N 9/02 | (2006.01) |
| G01F 22/00 | (2006.01) |
| G07C 5/08 | (2006.01) |
| B60P 1/00 | (2006.01) |
| G07C 5/00 | (2006.01) |

(52) U.S. Cl.
CPC .............. G01N 9/02 (2013.01); B60P 1/00 (2013.01); G01F 22/00 (2013.01); G07C 5/008 (2013.01); G07C 5/085 (2013.01); G01N 2009/022 (2013.01); G01N 2009/024 (2013.01)

(58) Field of Classification Search
CPC .......... E02F 9/264; E02F 3/431; G01G 19/10; G01G 23/37
USPC ................. 702/127, 137, 173–175
See application file for complete search history.

(56) References Cited

U.S. PATENT DOCUMENTS

| | | |
|---|---|---|
| 6,668,157 B1 | 12/2003 | Takeda et al. |
| 8,515,627 B2 * | 8/2013 | Marathe ............. E02F 9/264 701/124 |
| 8,838,331 B2 | 9/2014 | Jensen |
| 2009/0062993 A1 | 3/2009 | Morey et al. |
| 2009/0088961 A1 | 4/2009 | Morey et al. |
| 2012/0136542 A1 | 5/2012 | Upcroft et al. |
| 2014/0288771 A1 | 9/2014 | Li |

OTHER PUBLICATIONS

Holt-Caterpillar, "Performance Handbook", Mining and Earthmoving, Edition 41, Sec 22, P. 1-16, 2012, https://www.holtcat.com/Documents/PDFs/2012PerformanceHandbook/Mining%20&%20Earthmoving%20-%20Sec%2022.pdf.

* cited by examiner

*Primary Examiner* — An H Do
(74) *Attorney, Agent, or Firm* — Klintworth & Rozenblat IP LLP

(57) ABSTRACT

A load verification system and method may be used to assess the loading of material from a loading work vehicle having a load bucket to a haulage work vehicle having a load bin. The system includes at least one volume sensor coupled to the loading work vehicle that observes a volume of material in at least one of the load bucket and the load bin and generates a corresponding volume data signal. The system also includes a first controller onboard the loading work vehicle and a second controller onboard the haulage work vehicle. At least one of the first and second controllers: receives the volume data signal from the at least one volume sensor; receives a unique haulage work vehicle identifier; associates volume data of the corresponding volume data signal with the unique haulage work vehicle identifier; and stores in memory the associated volume data and haulage work vehicle identifier.

20 Claims, 7 Drawing Sheets

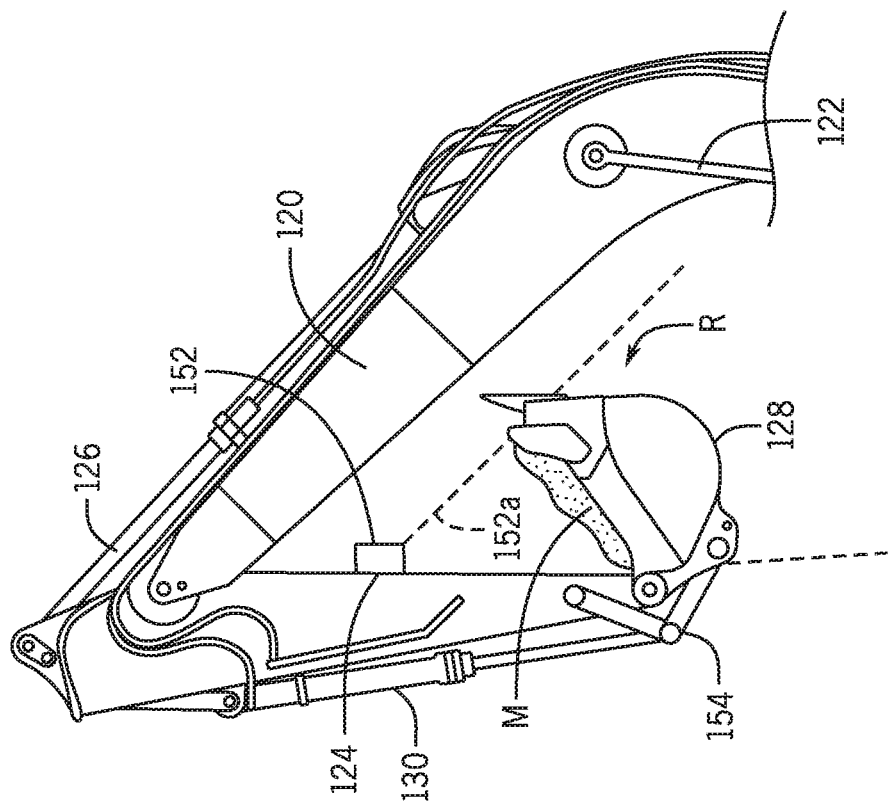
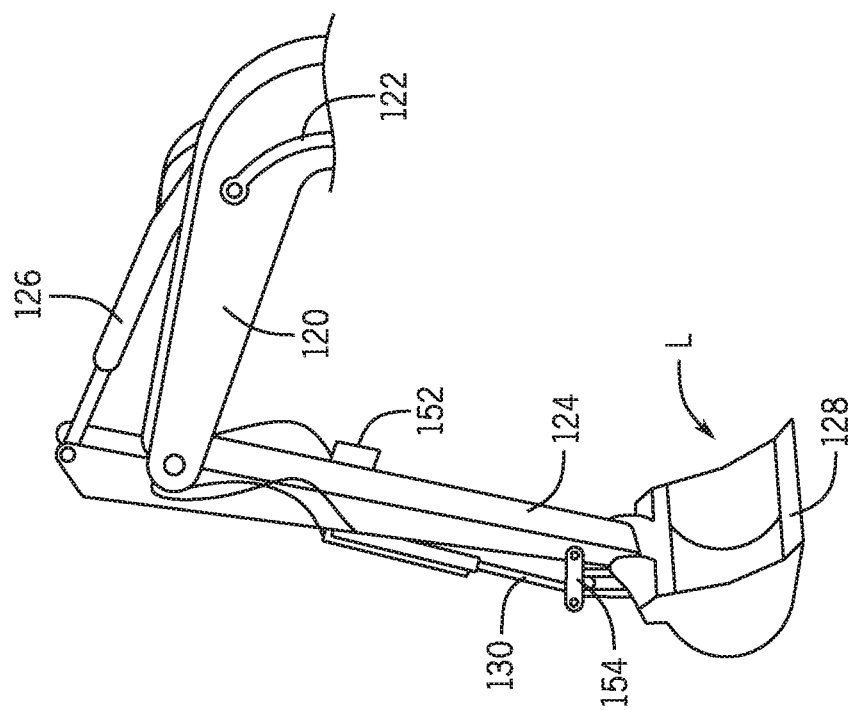
FIG. 1B
FIG. 1A

SYSTEM AND METHOD FOR LOAD EVALUATION

CROSS-REFERENCE TO RELATED APPLICATION(S)

Not applicable.

STATEMENT OF FEDERALLY SPONSORED RESEARCH OR DEVELOPMENT

Not applicable.

FIELD OF THE DISCLOSURE

This disclosure relates to work vehicles and to a load verification system that assesses the loading of material from a loading work vehicle to a haulage work vehicle.

BACKGROUND OF THE DISCLOSURE

In the construction industry, various work vehicles are operated to perform various tasks at a work site. For example, an articulated dump truck may be utilized to haul loads of material over rough terrain. An excavator or loader may be used to load material into a load bin of the articulated dump trunk. Currently, to measure a volume of material loaded into the articulated dump truck, an operator may need to rely on various estimates, for example, using various modeling techniques based on a rated capacity of the articulated dump truck, that may be less accurate than desired.

Load haulers may be compensated based on the volume of material carried over a work cycle, or, alternatively, load haulers may be paid based on the density of the materials hauled over the work cycle. In either case, an inaccurate estimated volume or density of materials moved may affect the hauling cost for the work performed at the job site. Moreover, a productivity of the loading and/or hauling operation (associated with the excavator or loader and/or the articulated dump truck) may be measured according to the volume or density of material moved by the machines within a period of time. Productivity assessments thus suffer in a similar manner from inaccurate loading/hauling estimates.

SUMMARY OF THE DISCLOSURE

The disclosure provides a system and method for evaluating a loading of a haulage work vehicle by a loading work vehicle.

In one aspect the disclosure provides a load evaluation system for assessing the loading of material from a loading work vehicle having a load bucket to a haulage work vehicle having a load bin. The load evaluation system includes at least one volume sensor coupled to the loading work vehicle and configured to sense a volume of material in at least one of the load bucket and the load bin and generate a corresponding volume data signal. The load evaluation system includes a first controller onboard the loading work vehicle and a second controller onboard the haulage work vehicle. At least one of the first and second controllers is configured to: receive the volume data signal from the at least one volume sensor; receive a unique haulage work vehicle identifier; associate volume data of the corresponding volume data signal with the unique haulage work vehicle identifier; and store in memory the associated volume data and haulage work vehicle identifier.

In another aspect the disclosure provides a load evaluation method for assessing the loading of material from a loading work vehicle having a load bucket to a haulage work vehicle having a load bin. The method includes sensing a volume of material in at least one of the load bucket and the load bin with at least one volume sensor and generating a corresponding volume data signal; receiving, by a first controller onboard the loading work vehicle, the volume data signal from the at least one volume sensor; transmitting, by the first controller, volume data corresponding to the volume data signal to a second controller onboard the haulage work vehicle; associating, by the second controller, the volume data of the corresponding volume data signal with a unique haulage work vehicle identifier; and storing in memory the associated volume data and haulage work vehicle identifier.

The details of one or more embodiments are set forth in the accompanying drawings and the description below. Other features and advantages will become apparent from the description, the drawings, and the claims.

BRIEF DESCRIPTION OF THE DRAWINGS

FIG. 1A is a schematic partial illustration of a boom and bucket of the example loading work vehicle in a load position;

FIG. 1B is a schematic partial illustration of the boom and bucket of the example loading work vehicle in a rollback position;

Like reference symbols in the various drawings indicate like elements.

DETAILED DESCRIPTION

Figure 1:
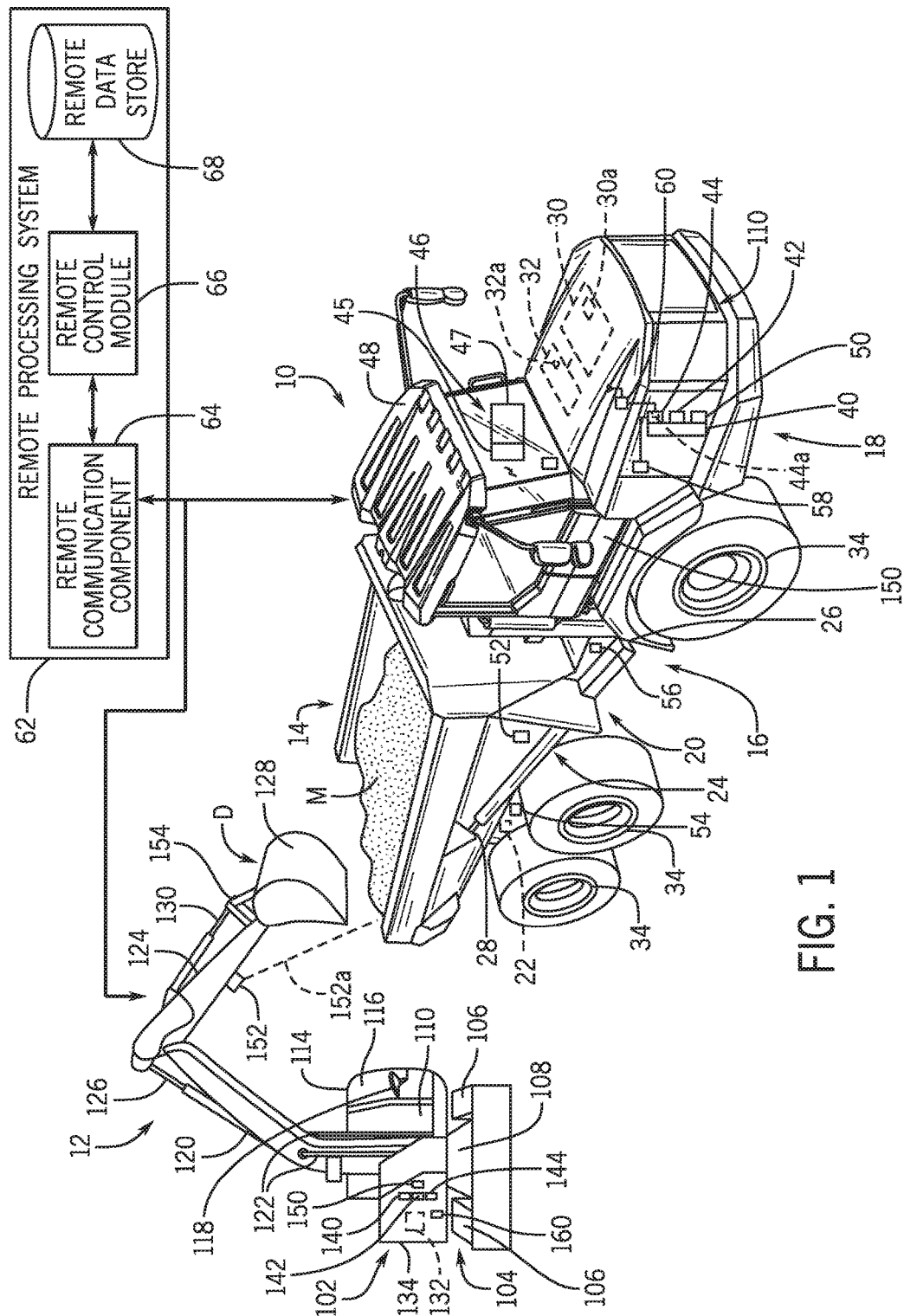
FIG. 1 is a perspective view of an example haulage work vehicle in the form of an articulated dump truck and an example loading work vehicle in the form of an excavator, in which the disclosed load evaluation system and method may be used.

The following describes one or more example embodiments of the disclosed system and method, as shown in the accompanying figures of the drawings described briefly above. Various modifications to the example embodiments may be contemplated by one of skill in the art.

As used herein, unless otherwise limited or modified, lists with elements that are separated by conjunctive terms (e.g., "and") and that are also preceded by the phrase "one or more of" or "at least one of" indicate configurations or arrangements that potentially include individual elements of the list, or any combination thereof. For example, "at least one of A, B, and C" or "one or more of A, B, and C" indicates the possibilities of only A, only B, only C, or any combination of two or more of A, B, and C (e.g., A and B; B and C; A and C; or A, B, and C).

As used herein, the term module refers to any hardware, software, firmware, electronic control component, processing logic, and/or processor device, individually or in any combination, including without limitation: application specific integrated circuit (ASIC), an electronic circuit, a processor (shared, dedicated, or group) and memory that executes one or more software or firmware programs, a combinational logic circuit, and/or other suitable components that provide the described functionality.

Embodiments of the present disclosure may be described herein in terms of functional and/or logical block components and various processing steps. It should be appreciated that such block components may be realized by any number of hardware, software, and/or firmware components configured to perform the specified functions. For example, an embodiment of the present disclosure may employ various integrated circuit components, e.g., memory elements, digital signal processing elements, logic elements, look-up tables, or the like, which may carry out a variety of functions under the control of one or more microprocessors or other control devices. In addition, those skilled in the art will appreciate that embodiments of the present disclosure may be practiced in conjunction with any number of work vehicles, and that the articulated dump truck and the excavator described herein are merely one exemplary embodiment of the present disclosure.

For the sake of brevity, conventional techniques related to signal processing, data transmission, signaling, control, and other functional aspects of the systems (and the individual operating components of the systems) may not be described in detail herein. Furthermore, the connecting lines shown in the various figures contained herein are intended to represent example functional relationships and/or physical couplings between the various elements. It should be noted that many alternative or additional functional relationships or physical connections may be present in an embodiment of the present disclosure.

The following describes one or more example implementations of the disclosed system for load evaluation for a haulage work vehicle, as shown in the accompanying figures of the drawings described briefly above. Generally, the disclosed systems (and work vehicles in which they are implemented) provide for improved load evaluation as compared to conventional systems by sensing a volume in a bucket of a loading work vehicle and/or a volume in a load bin of the haulage work vehicle, and generating sensor signals based thereon. These volume data signals are processed to determine a volume in the bucket and/or the load bin, and are used to more accurately calculate an amount or volume of material hauled by the haulage work vehicle during a work cycle. Further, by measuring the volume in the bucket and/or the load bin, the density may be calculated for each bucket load of the loading work vehicle over a loading cycle of the haulage work vehicle. By more accurately calculating the volume or density of the load, haulage and loading costs may be more accurately assessed, as may measurements of the productivity of the work vehicles.

Discussion herein may sometimes focus on the example application of the load evaluation system for an excavator. In other applications, other configurations are also possible. For example, work vehicles in some embodiments may be configured as various loaders, including wheel loaders, tractor loaders, crawler loaders or similar machines. Further, work vehicles may be configured as machines other than construction vehicles, including machines from the agriculture, forestry and mining industries, such as tractors, combines, harvesters, feller bunchers, and so on. Thus, the configuration of the load evaluation system for use with an excavator is merely an example. Similarly, the load evaluation system is described herein with respect to a haulage work vehicle in the form of an articulated dump truck. However, the load evaluation system may be employed with various other haulage machines (e.g., various fixed-chassis dump trucks, commodity carts, or other vehicles with carrying bins and vessels).

Generally, the disclosed load evaluation system includes a volume sensor mounted to an arm coupled to a boom of the loading work vehicle. In one example, the volume sensor is mounted on the boom arm (e.g., a stick boom) near the bucket, such that a field of view of the sensor includes the bucket, but may also include the load bin of the haulage work vehicle based on a position of the arm relative to the haulage work vehicle. Thus, the volume sensor is coupled to the loading work vehicle to observe the volume of materials in the bucket and the volume of materials in the load bin and generate volume data signals based thereon. In various embodiments, the volume sensor comprises a camera assembly, that captures image data of the bucket and/or load bin. In other embodiments, the volume sensor is a radar, lidar or similar sensor. In some embodiments, a combination of a camera assembly and a radar, lidar or similar sensor may be employed. Further, in other embodiments, one or more hydraulic pressure sensors may be employed to observe a pressure within one or more hydraulic cylinders associated with the loading work vehicle and to generate sensor signals based on the observation. The pressure sensor signals are indicative of a mass associated with a load in the bucket of the loading work vehicle. In some embodiments, one or more accelerometers may be employed to observe an acceleration acting on the bucket of the loading work vehicle and to generate sensor signals based on this observation. The acceleration sensor signals are also indicative of a mass associated with a load in the bucket of the loading work vehicle.

Generally, a controller of the loading work vehicle acquires the volume data signal based on a position of the bucket. For example, when the bucket is determined to be in a rollback position, the controller acquires a volume data signal. The volume data signal is processed by the controller, and a volume of material within the bucket and/or load bin as acquired by the volume sensor is transmitted by the controller of the loading work vehicle to the haulage work vehicle as volume data.

A controller of the haulage work vehicle receives the volume data, and optionally, receives a mass data signal from a load sensor coupled to the load bin. The controller of the haulage work vehicle associates the volume data and a determined mass in the load bin with a unique identifier associated with the haulage work vehicle. This associated data is stored in a memory or datastore. The controller of the haulage work vehicle also calculates a density based on the current volume data and mass data, and stores this data with the associated data in the memory. The controller repeats this process over a loading cycle of the haulage work vehicle, such that upon completion of the loading cycle, the memory or datastore includes the volume, the mass and the density for the particular haulage work vehicle for each of the particular bucket loads or load cycles. This data may be transmitted by the controller to a remote processing system, such as a telematics system, to enable access to this data by a remote user. The controller may also calculate a total density for the loading cycle, which may also be transmitted to the remote processing system.

The controller may also calculate incremental change data between each of the bucket load cycles. For example, the controller may calculate incremental changes in density, volume, etc. between each load cycle of the loading work vehicle. This data may also be transmitted to the remote processing system.

As noted above, the disclosed load evaluation system and method may be utilized with regard to various work vehicles, including articulated dump trucks, loaders, graders, tractors, combines, semi-truck haulers, etc. Referring to FIG. 1, in some embodiments, the disclosed load evaluation system may be used with a haulage work vehicle 10, such as an articulated dump truck (ADT), and a loading work vehicle 12, such as an excavator, to assess a volume of material loaded by the loading work vehicle 12 into the haulage work vehicle 10. In this example, the haulage work vehicle 10 includes a load bin 14 mounted to a vehicle frame 16. It will be understood that the configuration of the haulage work vehicle 10 having the load bin 14 is presented as an example only.

In the embodiment depicted, the vehicle frame 16 includes a first, front frame portion 18 and a second, rear frame portion 20, which are coupled together via an articulation joint (not shown) to enable pivotal movement between the front frame portion 18 and the rear frame portion 20. The load bin 14 is mounted to the rear frame portion 20 via coupling pins 22 that define a pivot point for the load bin 14. The load bin 14 defines a receptacle to receive a payload of materials.

One or more hydraulic cylinders 24 are mounted to the rear frame portion 20 and to the load bin 14, such that the hydraulic cylinders 24 may be driven or actuated in order to pivot the load bin 14 about the coupling pins 22. Generally, the haulage work vehicle 10 includes two hydraulic cylinders 24, one on a left side of the load bin 14 and one on a right side of the load bin 14 in a forward driving direction of the haulage work vehicle 10. It should be noted, however, that the haulage work vehicle 10 may have any number of hydraulic cylinders, such as one, three, etc. Each of the hydraulic cylinders 24 includes an end mounted to the rear frame portion 20 at a pin 26 and an end mounted to the load bin 14 at a pin 28. Upon activation of the hydraulic cylinders 24, the load bin 14 may be moved from a lowered, loaded position (FIG. 1) to a raised, unloaded position (not shown) to dump a payload contained within the load bin 14.

Thus, in the embodiment depicted, the load bin 14 is pivotable vertically relative to a horizontal axis by the one or more hydraulic cylinders 24. In other configurations, other movements of a load bin may be possible. Further, in some embodiments, a different number or configuration of hydraulic cylinders or other actuators may be used. Thus, it will be understood that the configuration of the load bin 14 is presented as an example only. In this regard, a load bin (e.g., the load bin 14) may be generally viewed as a receptacle that is pivotally attached to a vehicle frame. Similarly, a coupling pin (e.g., the coupling pins 22) may be generally viewed as a pin or similar feature effecting pivotal attachment of a load bin to a vehicle frame. In this light, a tilt actuator (e.g., the hydraulic cylinders 24) may be generally viewed as an actuator for pivoting a receptacle with respect to a vehicle frame.

The haulage work vehicle 10 includes a source of propulsion, such as an engine 30. The engine 30 supplies power to a transmission 32. In one example, the engine 30 is an internal combustion engine, such as a diesel engine, that is controlled by an engine control module 30a. It should be noted that the use of an internal combustion engine is merely an example, as the propulsion device may be a fuel cell, an electric motor, a hybrid-gas electric motor, etc.

The transmission 32 transfers the power from the engine 30 to a suitable driveline coupled to one or more driven wheels 34 (and tires) of the haulage work vehicle 10 to enable the haulage work vehicle 10 to move. As is known to one skilled in the art, the transmission 32 may include a suitable gear transmission, which may be operated in a variety of ranges containing one or more gears, including, but not limited to a park range, a neutral range, a reverse range, a drive range, a low range, etc. In one example, the transmission 32 is controlled by a transmission control module 32a.

The haulage work vehicle 10 also includes one or more pumps 40, which may be driven by the engine 30 of the haulage work vehicle 10. Flow from the pumps 40 may be routed through various control valves 42 and various conduits (e.g., flexible hoses) in order to drive the hydraulic cylinders 24. Flow from the pumps 40 may also power various other components of the haulage work vehicle 10. The flow from the pumps 40 may be controlled in various ways (e.g., through control of the various control valves 42), in order to cause movement of the hydraulic cylinders 24, and thus, movement of the load bin 14 relative to the vehicle frame 16. In this way, for example, a movement of the load bin 14 between the lowered, loaded position (FIG. 1) and the raised, unloaded position (not shown) may be implemented by various control signals to the pumps 40, control valves 42, and so on.

Generally, a haulage controller 44 (or multiple controllers) may be provided, for control of various aspects of the operation of the haulage work vehicle 10, in general. The haulage controller 44 (or others) may be configured as a computing device with associated processor devices and memory architectures, as a hard-wired computing circuit (or circuits), as a programmable circuit, as a hydraulic, electrical or electro-hydraulic controller, or otherwise. As such, the haulage controller 44 may be configured to execute various computational and control functionality with respect to the haulage work vehicle 10 (or other machinery). In some embodiments, the haulage controller 44 may be configured to receive input signals in various formats (e.g., as hydraulic signals, voltage signals, current signals, and so on), and to output command signals in various formats (e.g., as hydraulic signals, voltage signals, current signals, mechanical movements, and so on). In some embodiments, the haulage controller 44 (or a portion thereof) may be configured as an assembly of hydraulic components (e.g., valves, flow lines, pistons and cylinders, and so on), such that control of various devices (e.g., pumps or motors) may be effected with, and based upon, hydraulic, mechanical, or other signals and movements.

The haulage controller 44 may be in electronic, hydraulic, mechanical, or other communication with various other systems or devices of the haulage work vehicle 10 (or other machinery). For example, the haulage controller 44 may be in electronic or hydraulic communication with various actuators, sensors, and other devices within (or outside of) the haulage work vehicle 10, including various devices associated with the pumps 40, control valves 42, and so on. The haulage controller 44 may communicate with other systems or devices (including other controllers, such as a loader controller 144 of the loading work vehicle 12) in various known ways, including via a CAN bus (not shown) of the haulage work vehicle 10, via wireless or hydraulic communication means, or otherwise. An example location for the haulage controller 44 is depicted in FIG. 1. It will be understood, however, that other locations are possible including other locations on the haulage work vehicle 10, or various remote locations.

In some embodiments, the haulage controller 44 may be configured to receive input commands and to interact with an operator via a human-machine interface 46, which may be disposed inside a cab 48 of the haulage work vehicle 10 for easy access by the operator. The human-machine interface 46 may be configured in a variety of ways. In some embodiments, the human-machine interface 46 may include an input device 45 comprising one or more joysticks, various switches or levers, one or more buttons, a touchscreen interface that may be overlaid on a display 47, a keyboard, a speaker, a microphone associated with a speech recognition system, or various other human-machine interface devices. The human-machine interface 46 also includes the display 47, which may be implemented as a flat panel display or other display type that is integrated with an instrument panel or console of the haulage work vehicle 10. Those skilled in the art may realize other techniques to implement the display 47 in the haulage work vehicle 10.

Various sensors may also be provided to observe various conditions associated with the haulage work vehicle 10. In some embodiments, various sensors 50 (e.g., pressure, flow or other sensors) may be disposed near the pumps 40 and control valves 42, or elsewhere on the haulage work vehicle 10. For example, sensors 50 may include one or more pressure sensors that observe a pressure within the hydraulic circuit, such as a pressure associated with at least one of the one or more hydraulic cylinders 24. The sensors 50 may also observe a pressure associated with the pumps 40. In some embodiments, various sensors may be disposed near the load bin 14. For example, sensors 52 (e.g. load sensors) may be disposed on or coupled near the load bin 14 in order to measure parameters including the load in the load bin 14 and so on. For example, sensors 52 may observe a mass of the material M in the load bin 14 and generate a mass data signal based thereon.

Various sensors 54 may also be disposed on or near the rear frame portion 20 in order to measure parameters, such as an incline or slope of the rear frame portion 20, and so on. In some embodiments, the sensors 54 may include an inclinometer coupled to or near the rear frame portion 20, etc. In certain embodiments, the sensors 54 may be microelectromechanical sensors (MEMS) that observe a force of gravity and an acceleration associated with the haulage work vehicle 10. In addition, various sensors 56 are disposed near the rear frame portion 20 in order to observe an orientation of the load bin 14 relative to the rear frame portion 20. In some embodiments, the sensors 56 include angular position sensors coupled between the rear frame portion 20 and the load bin 14 in order to detect the angular orientation of the load bin 14 relative to the rear frame portion 20.

The various components noted above (or others) may be utilized to control movement of the load bin 14 via control of the movement of the one or more hydraulic cylinders 24. Each of the sensors 50, 52, 54 and 56, and the human-machine interface 46, may be in communication with the haulage controller 44 via a suitable communication architecture, such as the CAN bus associated with the haulage work vehicle 10.

The haulage work vehicle 10 includes a vehicle communication component 60. The vehicle communication component 60 enables communication between the haulage controller 44, the loader controller 144 and a remote processing system or remote system 62. The vehicle communication component 60 comprises any suitable system for receiving data from and transmitting data to the loader controller 144 and/or remote system 62. For example, the vehicle communication component 60 may include a radio configured to receive data transmitted by modulating a radio frequency (RF) signal from a remote station (not shown) as is well known to those skilled in the art. For example, the remote station (not shown) may be part of a cellular telephone network and the data may be transmitted according to the long-term evolution (LTE) standard. The vehicle communication component 60 also transmits data to the remote station (not shown) to achieve bi-directional communications. However, other techniques for transmitting and receiving data may alternately be utilized. In one example, the vehicle communication component 60 achieves bi-directional communications with the loader controller 144 and/or the remote system 62 over Bluetooth®, satellite or by utilizing a Wi-Fi standard, i.e., one or more of the 802.11 standards as defined by the Institute of Electrical and Electronics Engineers ("IEEE"), as is well known to those skilled in the art. Thus, the vehicle communication component 60 comprises a Bluetooth® transceiver, a satellite transceiver, a radio transceiver, a cellular transceiver, an LTE transceiver and/or a Wi-Fi transceiver.

In certain embodiments, the vehicle communication component 60 may be configured to encode data or generate encoded data. The encoded data generated by the vehicle communication component 60 may be encrypted. A security key may be utilized to decrypt and decode the encoded data, as is appreciated by those skilled in the art. The security key may be a "password" or other arrangement of data that permits the encoded data to be decrypted. Alternatively, the remote station (not shown) may implement security protocols to ensure that communication takes place between the appropriate haulage work vehicle 10, the loading work vehicle 12 and the remote system 62.

In certain embodiments, the vehicle communication component 60 is in communication with the remote system 62. In one example, the remote system 62 comprises the JDLink™ telematics system commercially available from Deere & Company of Moline, Ill.; however, the remote system 62 may comprise any suitable telematics system. The remote system 62 includes a remote communication component 64, a remote control module 66 and one or more remote data stores 68. The remote communication component 64 comprises any suitable system for receiving data from and transmitting data to the vehicle communication component 60 and a vehicle communication component 160 associated with the loading work vehicle 12. For example, the remote communication component 64 may include a radio configured to receive data transmitted by modulating a radio frequency (RF) signal from a remote station (not shown) as is well known to those skilled in the art. For example, the remote station (not shown) may be part of a cellular telephone network and the data may be transmitted according to the long-term evolution (LTE) standard. The remote communication component 64 also transmits data to the remote station (not shown) to achieve bi-directional communications. However, other techniques for transmitting and receiving data may alternately be utilized. For example, the remote communication component 64 may achieve bi-directional communications with the vehicle communication component 60, 160 over Bluetooth®, satellite, or by utilizing a Wi-Fi standard, i.e., one or more of the 802.11 standards as defined by the Institute of Electrical and Electronics Engineers ("IEEE"), as is known to those skilled in the art. Thus, the remote communication component 64 comprises a Bluetooth® transceiver, a radio transceiver, a cellular transceiver, a satellite transceiver, an LTE transceiver and/or a Wi-Fi transceiver.

The remote communication component 64 may also be configured to encode data or generate encoded data. The encoded data generated by the remote communication component 64 may be encrypted. A security key may be utilized to decrypt and decode the encoded data, as is appreciated by those skilled in the art. The security key may be a "password" or other arrangement of data that permits the encoded data to be decrypted.

The remote control module 66 is in communication with the remote communication component 64 and the one or more remote data stores 68 over a suitable interconnection architecture or arrangement that facilitates transfer of data, commands, power, etc. The remote control module 66 may also be in communication with one or more remote users via a portal, such as a web-based portal. The remote control module 66 may be configured as a computing device with associated processor devices and memory architectures, as a hard-wired computing circuit (or circuits), as a programmable circuit, or otherwise. The remote control module 66 receives data communicated from the vehicle communication component 60 and sets data, such as total density data, incremental change data and loading cycle data for a particular haulage work vehicle 10 for one or more of the remote data stores 68. In one example, at least one of the one or more remote data stores 68 stores data, such as the total density data, incremental change data and loading cycle data for the haulage work vehicle 10. The total density data, incremental change data and loading cycle data for the haulage work vehicle 10 may be stored in any desired format, and may comprise one or more tables. The tables may be indexed by haulage work vehicle identifier, etc. to enable retrieval of the total density data, incremental change data and/or loading cycle data upon a request received from a remote user in communication with the remote control module 66 via the web-based portal.

With continued reference to FIG. 1, the loading work vehicle 12 includes an upper frame 102 pivotally mounted to an undercarriage 104. The upper frame 102 may be pivotally mounted on the undercarriage 104 by means of a swing pivot 108. The upper frame 102 is rotatable about 360 degrees relative to the undercarriage 104 on the swing pivot 108. A hydraulic motor (not shown) may drive a gear train (not shown) for pivoting the upper frame 102 about the swing pivot 108.

The undercarriage 104 may include a pair of ground-engaging tracks 106 on opposite sides of the undercarriage 104 for moving along the ground. Alternatively, the loading work vehicle 12 may include wheels for engaging the ground. The upper frame 102 includes a cab 110 in which the machine operator controls the machine. The cab 110 includes a loader human-machine interface 114. The loader human-machine interface 114 may be configured in a variety of ways. In some embodiments, the loader human-machine interface 114 includes a loader input device 116 comprising one or more joysticks, various switches or levers, one or more buttons, a touchscreen interface that may be overlaid on a display 118, a keyboard, a speaker, a microphone associated with a speech recognition system, control pedals or various other human-machine interface devices. The loader human-machine interface 114 also includes the display 118, which may be implemented as a flat panel display or other display type that is integrated with an instrument panel or console of the loading work vehicle 12. Those skilled in the art may realize other techniques to implement the display 118 in the loading work vehicle 12. The operator may actuate one or more devices of the loader human-machine interface 114 for purposes of operating the loading work vehicle 12 and/or for initiating a load assessment.

The loading work vehicle 12 also includes a large boom 120 that extends from the upper frame 102 adjacent to the cab 110. The boom 120 is rotatable about a vertical arc by actuation of a pair of boom hydraulic cylinders 122. A dipper stick or arm 124 is rotatably mounted at one end of the boom 120 and its position is controlled by a hydraulic cylinder 126. The opposite end of the boom 120 is coupled to the upper frame 102. At the end opposite the boom 120, the dipper stick or arm 124 is mounted to an excavator bucket 128 that is pivotable relative to the arm 124 by means of a hydraulic cylinder 130.

The upper frame 102 of the loading work vehicle 12 includes an outer shell cover to protect a propulsion system, such as an engine 132. At an end opposite the cab 110, the upper frame 102 includes a counterweight body 134. The counterweight body 134 comprises a housing filled with material to add weight to the machine and offset a load collected in the bucket 128. The offset weight may improve the digging performance of the loading work vehicle 12.

The loading work vehicle 12 also includes one or more pumps 140, which may be driven by the engine 132 of the loading work vehicle 12. Flow from the pumps 140 may be routed through various control valves 142 and various conduits (e.g., flexible hoses) in order to drive the hydraulic cylinders 122, 126, 130. Flow from the pumps 140 may also power various other components of the loading work vehicle 12. The flow from the pumps 140 may be controlled in various ways (e.g., through control of the various control valves 142), in order to cause movement of the hydraulic cylinders 122, 126, 130, and thus, movement of the bucket 128 relative to the upper frame 102. In this way, for example, a movement of the bucket 128 between a load position L to load a material M (FIG. 1A) and a rollback position R to carry the material M (FIG. 1B) may be implemented by various control signals to the pumps 140, control valves 142, and so on.

Generally, the loader controller 144 (or multiple controllers) may be provided, for control of various aspects of the operation of the loading work vehicle 12, in general. The loader controller 144 (or others) may be configured as a computing device with associated processor devices and memory architectures, as a hard-wired computing circuit (or circuits), as a programmable circuit, as a hydraulic, electrical or electro-hydraulic controller, or otherwise. As such, the loader controller 144 may be configured to execute various computational and control functionality with respect to the loading work vehicle 12 (or other machinery). In some embodiments, the loader controller 144 may be configured to receive input signals in various formats (e.g., as hydraulic signals, voltage signals, current signals, and so on), and to output command signals in various formats (e.g., as hydraulic signals, voltage signals, current signals, mechanical movements, and so on). In some embodiments, the loader controller 144 (or a portion thereof) may be configured as an assembly of hydraulic components (e.g., valves, flow lines, pistons and cylinders, and so on), such that control of various devices (e.g., pumps or motors) may be effected with, and based upon, hydraulic, mechanical, or other signals and movements.

The loader controller 144 may be in electronic, hydraulic, mechanical, or other communication with various other systems or devices of the loading work vehicle 12 (or other machinery). For example, the loader controller 144 may be in electronic or hydraulic communication with various actuators, sensors, and other devices within (or outside of) the loading work vehicle 12, including various devices associated with the pumps 140, control valves 142, and so on. The loader controller 144 may communicate with other systems or devices (including other controllers, such as the haulage controller 44 of the haulage work vehicle 10) in various known ways, including via a CAN bus (not shown) of the loading work vehicle 12, via wireless or hydraulic communication means, or otherwise. An example location for the loader controller 144 is depicted in FIG. 1. It will be understood, however, that other locations are possible including other locations on the loading work vehicle 12, or various remote locations. The loader controller 144 receives input commands and interacts with the operator via the loader human-machine interface 114.

Various sensors may also be provided to observe various conditions associated with the loading work vehicle 12. In some embodiments, various sensors 150 (e.g., pressure, flow or other sensors) may be disposed near the pumps 140 and control valves 142, or elsewhere on the loading work vehicle 12. For example, sensors 150 may include one or more pressure sensors that observe a pressure within the hydraulic circuit, such as a pressure associated with at least one of the one or more hydraulic cylinders 122, 126, 130 and generate sensor signals based the observation. Based on the pressure observed within the hydraulic cylinders 122, 126, 130, the loader controller 144 determines a mass of a load within the bucket 128. The sensors 150 may also observe a pressure associated with the pumps 140. In some embodiments, various sensors may be disposed near the bucket 128. For example, one or more accelerometers may be employed to observe an acceleration acting on the bucket 128 of the loading work vehicle 12 and to generate sensor signals based on this observation. The loader controller 144 receives these sensor signals and processes the sensor signals to determine a mass of a load within the bucket 128.

A sensor 152 (e.g. volume sensor) may be disposed on or coupled to the arm 124 in order to measure parameters including the volume of the material M (FIG. 1B) in the bucket 128 and/or a volume of material M within the load bin 14 (FIG. 1) and so on. It should be noted that the position of the sensor 152 in FIGS. 1-1B is merely exemplary, as the sensor 152 may be mounted at any desired position on the loading work vehicle 12 to observe the volume of the material M (FIG. 1B) in the bucket 128 and/or a volume of material M within the load bin 14 (FIG. 1), and generate sensor signals based thereon. In addition, the loading work vehicle 12 may include more than one sensor 152 to observe the volume of material in the load bin 14 and the bucket 128.

In one example, the sensor 152 includes a camera assembly, which observes an area that includes the bucket 128, when the bucket 128 is in the rollback position R (FIG. 1B), and observes an area that includes the load bin 14, when the bucket 128 is in a dump position D (FIG. 1) and generates image data based thereon. It should be noted that while the following description refers to a "camera assembly" any suitable visual sensor any be employed to obtain an imaged area that may include the bucket 128 and/or load bin 14. Moreover, the sensor 152 may comprise a lidar, radar or similar sensor that observes an object, such as the bucket 128 and/or load bin 14, and generates sensor signals based thereon that indicate a volume in the bucket 128 and/or load bin 14. In addition, the sensor 152 may comprise a combination of sensors, such as a camera assembly, a lidar and a radar.

In this example, with reference to FIG. 1B, the sensor 152 is mounted to or associated with the loading work vehicle 12 (or otherwise positioned) in order to capture images at least of a field of view 152a, which in this example, includes the bucket 128 of the loading work vehicle 12 when the bucket 128 is in the rollback position R and the load bin 14 of the haulage work vehicle 10 when the bucket 128 is in the dump position D. The sensor 152 may be in electronic (or other) communication with the loader controller 144 (or other devices) and may include various numbers of cameras of various types. In certain embodiments, the sensor 152 may include a color camera capable of capturing color images. In other embodiments, the sensor 152 may include an infrared camera to capture infrared images. In certain embodiments, the sensor 152 may include a grayscale camera to capture grayscale images. In other embodiments, the sensor 152 may include a stereo camera assembly capable of capturing stereo images. For example, the sensor 152 may include a stereo camera with two or more lenses and image sensors, or multiple cameras arranged to capture stereoscopic images of the field of view 152a, including the volume of material M within the bucket 128 and/or the load bin 14 within the field of view 152a.

Images may be captured by the sensor 152 according to various timings or other considerations, and the image data or image streams may include a timestamp. In certain embodiments, for example, the sensor 152 may capture images continuously based on a position of the bucket 128, such as the position of the bucket 128 in the rollback position R (FIG. 1B) or the dump position D (FIG. 1). In certain embodiments, embedded control system (not shown) for the sensor 152 may cause the sensor 152 to capture images of the field of view 152a at regular time intervals as loading work vehicle 12 executes a load cycle. In addition, one or more input devices of the loader human-machine interface 114 may also be used to cause the sensor 152 to capture images of the field of view 152a.

The sensor 152 provides a source of local image data for the loader controller 144. It will be understood that various other sources of image data for the loader controller 144 may be available. For example, a portable electronic device (not shown) may provide a source of image data for the loader controller 144 (i.e. as a source of remote image data). The portable electronic device may be in communication with the loading work vehicle 12 to transmit data to a vehicle communication component 160 associated with the loading work vehicle 12 and to receive the data from the vehicle communication component 160. The portable electronic device is any suitable electronic device external to the loading work vehicle 12, including, but not limited to, a hand-held portable electronic device, such as a tablet computing device, mobile or smart phone, personal digital assistant, a laptop computing device, etc.

Various sensors 154 (e.g. bucket position sensors) may also be disposed on or near the bucket 128 in order to measure parameters, such as an orientation of the bucket 128 relative to the arm 124, such as whether the bucket 128 is in the load position L (FIG. 1A), the rollback position R (FIG. 1B) or the dump position D (FIG. 1). In some embodiments, the sensors 154 include angular position sensors coupled between the arm 124 and the bucket 128 in order to detect the angular orientation of the bucket 128 relative to the arm 124.

The various components noted above (or others) may be utilized to control movement of the bucket 128 via control of the movement of the one or more hydraulic cylinders 122, 126, 130. Accordingly, these components may be viewed as forming part of the control system for the loading work vehicle 12. Each of the sensors 150-154, the mass sensors, and the loader human-machine interface 114 are in communication with the loader controller 144 via a suitable communication architecture, such as a CAN bus.

The loading work vehicle 12 includes a vehicle communication component 160. The vehicle communication component 160 enables communication between the loader controller 144, the haulage controller 44 and the remote system 62. The vehicle communication component 160 comprises any suitable system for receiving data from and transmitting data to the haulage controller 44 and/or remote system 62. For example, the vehicle communication component 160 may include a radio configured to receive data transmitted by modulating a radio frequency (RF) signal from a remote station (not shown) as is well known to those skilled in the art. For example, the remote station (not shown) may be part of a cellular telephone network and the data may be transmitted according to the long-term evolution (LTE) standard. The vehicle communication component 160 also transmits data to the haulage controller 44 and/or remote system 62 to achieve bi-directional communications. However, other techniques for transmitting and receiving data may alternately be utilized. In one example, the vehicle communication component 160 achieves bi-directional communications with the haulage controller 44 and/or remote system 62 over Bluetooth®, satellite or by utilizing a Wi-Fi standard, i.e., one or more of the 802.11 standards as defined by the Institute of Electrical and Electronics Engineers ("IEEE"), as is well known to those skilled in the art. Thus, the vehicle communication component 160 comprises a Bluetooth® transceiver, a satellite transceiver, a radio transceiver, a cellular transceiver, an LTE transceiver and/or a Wi-Fi transceiver.

In certain embodiments, the vehicle communication component 160 may be configured to encode data or generate encoded data. The encoded data generated by the vehicle communication component 160 may be encrypted. A security key may be utilized to decrypt and decode the encoded data, as is appreciated by those skilled in the art. The security key may be a "password" or other arrangement of data that permits the encoded data to be decrypted. Alternatively, the remote station (not shown) may implement security protocols to ensure that communication takes place between the appropriate loading work vehicle 12, haulage work vehicle 10 and the remote system 62.

In various embodiments, each of the haulage controller 44 and the loader controller 144 include a respective load evaluation control module, haulage load evaluation control module 44a and loader evaluation control module 144a, respectively, embedded within the respective haulage controller 44 and the loader controller 144. In various embodiments, the loader evaluation control module 144a outputs current load volume data to the haulage controller 44 based on input received from the loader input device 116, sensor signals received from the sensors 154, sensor signals received from the sensor 152, and further based on the load evaluation system and method of the present disclosure. In various embodiments, the loader evaluation control module 144a outputs an end of loading cycle notification based on input received from the loader input device 116, and further based on the load evaluation system and method of the present disclosure.

In various embodiments, the haulage load evaluation control module 44a associates a haulage work vehicle 10 identifier with the current load volume data received from the loader controller 144 and stores the associated data in a datastore. The haulage load evaluation control module 44a also associates the haulage work vehicle 10 identifier with the current load volume data received from the loader controller 144 and sensor signals received from the sensor 50 and stores the associated data in a datastore. The haulage load evaluation control module 44a outputs incremental change data for the remote system 62 based on the associated data, and further based on the load evaluation system and method of the present disclosure. The haulage load evaluation control module 44a outputs total density data for the remote system 62 based on the associated data, and further based on the load evaluation system and method of the present disclosure. The haulage load evaluation control module 44a outputs loading cycle data for the remote system 62 based on the associated data, and further based on the load evaluation system and method of the present disclosure. The haulage load evaluation control module 44a also outputs an overload notification for the human-machine interface 46 based on the associated data, and further based on the load evaluation system and method of the present disclosure.

It should be understood that while the foregoing and the following description describe various processes being performed by a particular one of the haulage load evaluation control module 44a of the haulage controller 44 and the loader evaluation control module 144a of the loader controller 144, one or more of the following processes may be performed by the remote control module 66. Moreover, one or more of the processes performed by the haulage load evaluation control module 44a may be performed by the loader evaluation control module 144a, and vice versa.

Figure 2:
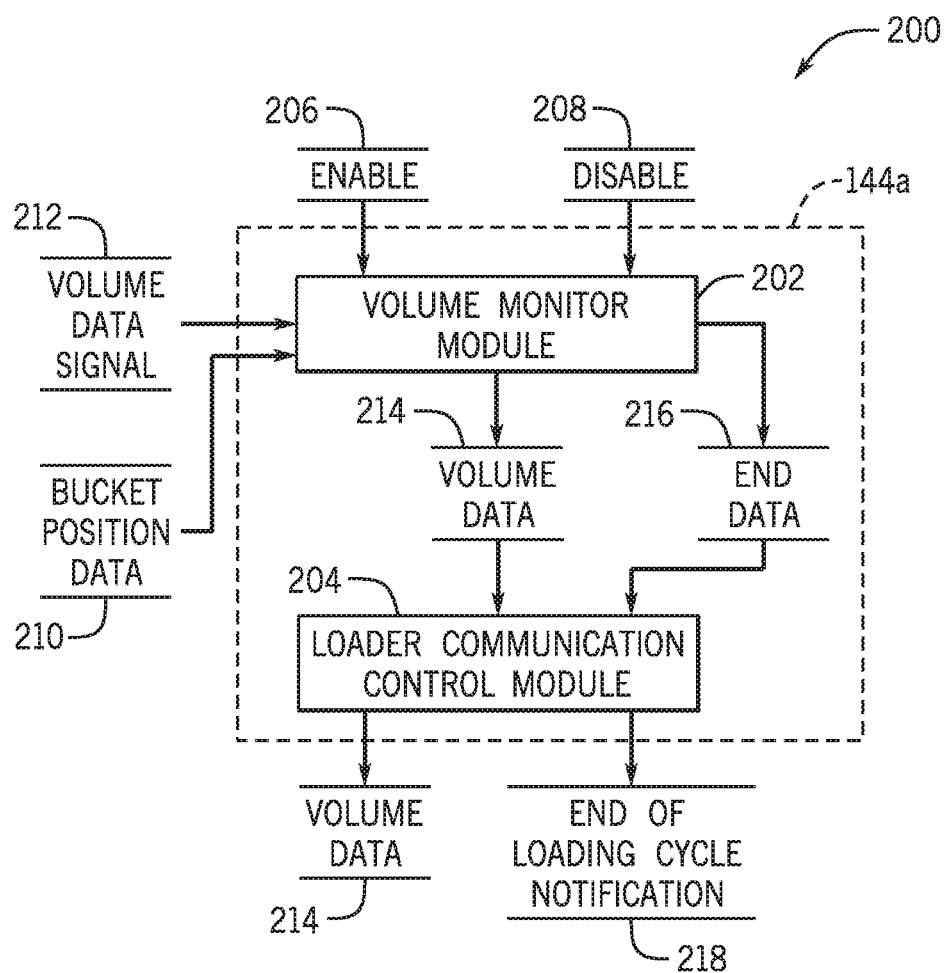
FIG. 2 is a dataflow diagram illustrating an example loader evaluation system for the loading work vehicle in accordance with various embodiments.

Referring now to FIG. 2, and with continuing reference to FIG. 1, a dataflow diagram illustrates various embodiments of a loader evaluation system 200 for the loading work vehicle 12, which may be embedded within the loader evaluation control module 144a of the loader controller 144. Various embodiments of the loader evaluation system 200 according to the present disclosure may include any number of sub-modules embedded within the loader controller 144. As may be appreciated, the sub-modules shown in FIG. 2 may be combined and/or further partitioned to similarly evaluate the load in the haulage work vehicle 10, to output the current load volume data and to output the end of loading cycle notification. Inputs to the loader evaluation system 200 may be received from the sensor 152 (FIG. 1), received from the sensor 154 (FIG. 1), received from the loader input device 116 (FIG. 1), received from other control modules (not shown) associated with the loading work vehicle 12, received from control modules (not shown) associated with the haulage work vehicle 10, and/or determined/modeled by other sub-modules (not shown) within the loader controller 144. In various embodiments, the loader evaluation control module 144a includes a volume monitor module 202 and a loader communication control module 204.

The volume monitor module 202 receives as input an enable 206 and a disable 208. In various embodiments, the enable 206 and the disable 208 are received as input commands to the loader input device 116 of the loader human-machine interface 114, and command the starting (enable) or stopping (disable) of a load evaluation. In one example, the loader human-machine interface 114 comprises a switch or button, which is actuated (e.g. depressed) to send a signal to enable (enable 206) the load evaluation and is re-actuated (e.g. re-depressed) to send a signal to disable (disable 208) the load evaluation. It will be understood, however, that any suitable device may be used to enable or disable the load evaluation, including a command received from the haulage controller 44.

Based on the receipt of the enable 206, the volume monitor module 202 receives as input bucket position data 210. The bucket position data 210 is the one or more sensor signals received from the sensors 154 of the loading work vehicle 12. The volume monitor module 202 processes the bucket position data 210 and determines whether the bucket 128 is in the load position L (FIG. 1A), such that the bucket 128 is able to be filled with materials. If the bucket 128 is in the load position L (FIG. 1A), the volume monitor module 202 continues to process the bucket position data 210 to determine whether the bucket 128 has been moved to the rollback position R (FIG. 1B) such that the bucket 128 is loaded with materials.

If the volume monitor module 202 determines that the bucket 128 is in the rollback position R (FIG. 1B), the volume monitor module 202 receives as input volume data signal 212. Alternatively, the volume monitor module 202 may receive the volume data signal 212 as input based on the determination that the bucket 128 is in the dump position D (FIG. 1). The volume data signal 212 is the sensor data received from the sensor 152. In this example, the volume data signal 212 comprises image data or an image stream.

The volume monitor module 202 processes the image data and determines whether the bucket 128 or the load bin 14 is within the image data. If either the bucket 128 or the load bin 14 is within the image data received from the sensor 152, the volume monitor module 202 processes the image data to determine a volume of material present within the bucket 128 or load bin 14. If the volume monitor module 202 does not identify the bucket 128 or the load bin 14 in the image data received from the sensor 152, the volume monitor module 202 may output an error, to the human-machine interface 46 and/or the loader human-machine interface 114, for example.

Based on this processing, the volume monitor module 202 sets volume data 214 for the loader communication control module 204. The volume data 214 is the current volume in the bucket 128 or the load bin 14 for the current load cycle of the loading work vehicle 12. A "load cycle" is defined as a movement of the bucket 128 from the load position L (FIG. 1A) and to the rollback position R (FIG. 1B). Stated another way, a load cycle is a single scoop of the bucket 128. After the determination of the volume data 214 for the current load cycle, the volume monitor module 202 processes the bucket position data 210 and determines whether the bucket 128 has returned to the load position L (FIG. 1A), such that the materials in the bucket 128 have been dumped into the load bin 14. If true, the volume monitor module 202 repeats the above process for each load cycle of the bucket 128 until the disable 208 is received.

Based on the receipt of the disable 208, the volume monitor module 202 sets end data 216 for the loader communication control module 204. The end data 216 indicates that a loading cycle has been completed. A "loading cycle" is defined as one or more load cycles of the bucket 128 to fill the load bin 14 of the haulage work vehicle 10 with materials. Stated another way, a loading cycle is generally a plurality of scoops of the bucket 128.

The loader communication control module 204 receives as input the volume data 214. The loader communication control module 204 outputs the volume data 214 for the haulage controller 44. The loader communication control module 204 also receives as input the end data 216. Based on the end data 216, the loader communication control module 204 outputs an end of loading cycle notification 218 for the haulage controller 44. The end of loading cycle notification 218 indicates that the loading cycle for the haulage work vehicle 10 is completed.

Figure 3:
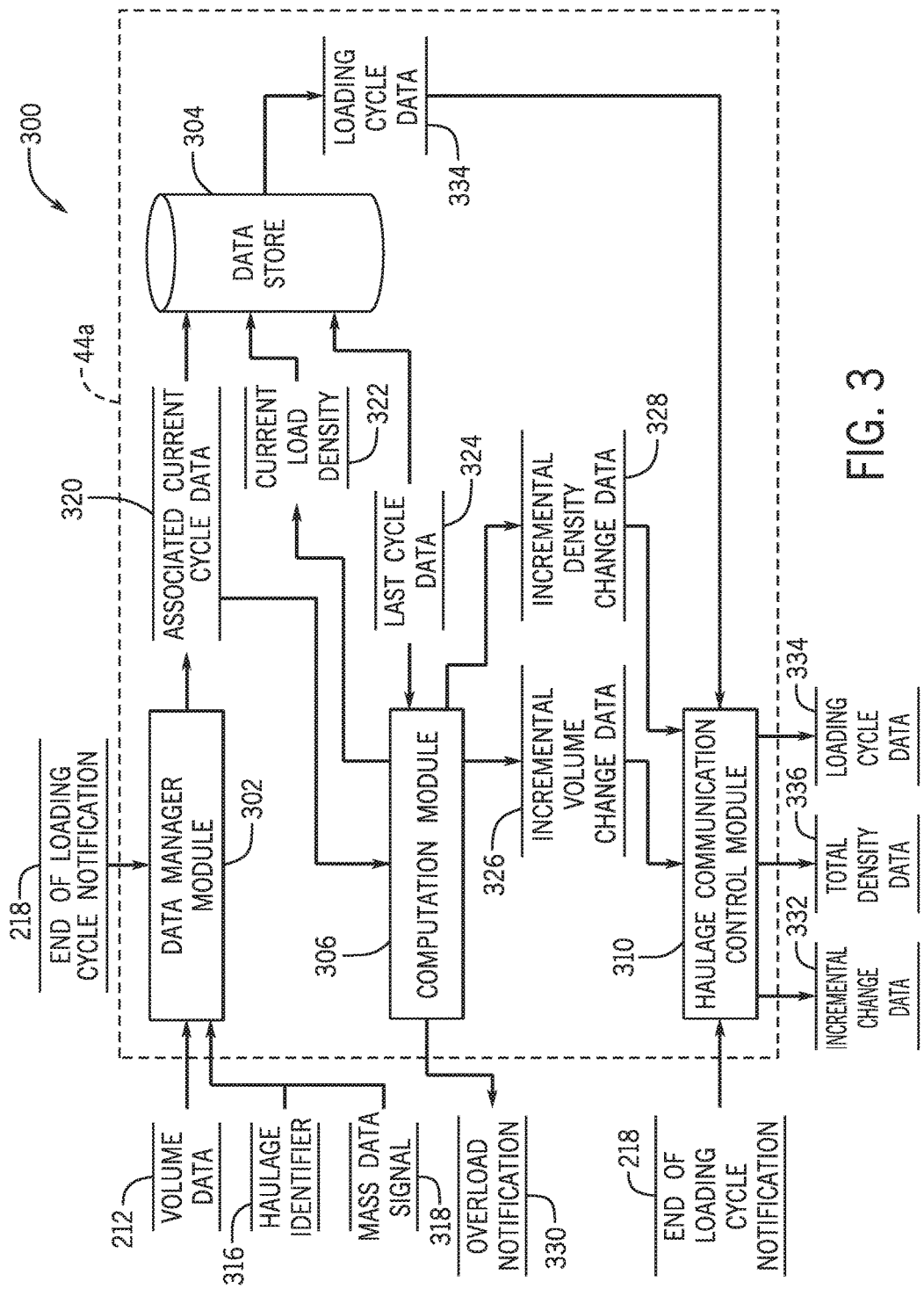
FIG. 3 is a dataflow diagram illustrating an example haulage load evaluation system for the haulage work vehicle in accordance with various embodiments.

Referring now to FIG. 3, and with continuing reference to FIG. 1, a dataflow diagram illustrates various embodiments of a haulage load evaluation system 300 for the haulage work vehicle 10, which may be embedded within the haulage load evaluation control module 44a of the haulage controller 44. Various embodiments of the haulage load evaluation system 300 according to the present disclosure may include any number of sub-modules embedded within the haulage controller 44. As may be appreciated, the sub-modules shown in FIG. 3 may be combined and/or further partitioned to similarly associate the volume data with a haulage identifier, to output an incremental change in the volume or the density between load cycles, to output total density data for a loading cycle, to output loading cycle data and to output an overload notification. Inputs to the haulage load evaluation system 300 may be received from the sensor 52 (FIG. 1), received from control modules (FIG. 2) associated with the loading work vehicle 12, received from control modules (not shown) associated with the haulage work vehicle 10, and/or determined/modeled by other sub-modules (not shown) within the haulage controller 44. In various embodiments, the haulage load evaluation control module 44a includes a data manager module 302, a datastore 304, a computation module 306 and a haulage communication control module 310.

The data manager module 302 receives as input the volume data 214 from the loader controller 144. Based on the received volume data 214, the data manager module 302 retrieves a unique haulage identifier 316 from a memory associated with the haulage load evaluation control module 44a. The unique haulage identifier 316 is stored in the memory associated with the haulage load evaluation control module 44a by the manufacturer, and comprises a unique default value, such as a vehicle identification number, which is associated with that particular haulage work vehicle 10. The data manager module 302 associates the received volume data 214 with the retrieved haulage identifier 316 and stores this associated data in the datastore 304.

In one example, based on the received volume data 214, the data manager module 302 receives as input a mass data signal 318 from the sensor 52. The data manager module 302 processes the mass data signal 318 to determine a mass of the payload in the load bin 14. The data manager module 302 associates the determined mass data with the haulage identifier 316 and the volume data 214 to generate associated current cycle data 320, which is stored in the datastore 304 and set for the computation module 306. Thus, the associated current cycle data 320 is the volume data 214 received from the loader controller 144 and the mass data determined from the mass data signal 318, which are each associated with a particular haulage work vehicle 10 identified by the haulage identifier 316 for a particular load cycle performed by the loading work vehicle 12. Thus, the associated current cycle data 320 comprises the data associated with the particular haulage work vehicle 10 for a particular load cycle performed by the loading work vehicle 12.

Based on the received volume data 214, the data manager module 302 determines whether the volume data 214 is associated with the start of a loading cycle by the loading work vehicle 12 into the haulage work vehicle 10. In one example, the data manager module 302 determines a start of a loading work cycle based on a prior receipt of the end of loading cycle notification 218 from the loader controller 144. Stated another way, if the data manager module 302 receives as input the end of loading cycle notification 218 and subsequently receives as input the volume data 214, the data manager module 302 determines the start of a new loading work cycle and stores the associated current cycle data 320 as the start of a new loading cycle in the datastore 304. Generally, if the data manager module 302 receives as input the volume data 214 subsequent to a previously received volume data 214, the data manager module 302 determines that the subsequently received volume data 214 is associated with the same loading cycle of the haulage work vehicle 10, and saves the generated associated current cycle data 320 as a subsequent load cycle for the current loading cycle in the datastore 304.

The data manager module 302 also receives as input the end of loading cycle notification 218 from the loader controller 144. Based on the receipt of the end of loading cycle notification 218, the data manager module 302 stores any subsequently received volume data 214 as the start of a new loading cycle for the haulage work vehicle 10 in the datastore 304. It should be noted that the end of loading cycle notification 218 is one example of how to aggregate the data associated with a particular loading cycle of the haulage work vehicle 10. It will be understood that other techniques may be employed, such as the use of time stamps, for example.

The datastore 304 stores the associated current cycle data 320 for each loading cycle of the haulage work vehicle 10 and also stores a current load density 322 for each load cycle. In one example, the datastore 304 is a relational database, and the data manager module 302 may store the associated current cycle data 320 and the current load density 322 in one or more tables associated with the datastore 304. For example, one or more of the tables in the datastore 304 may be indexed based on the haulage identifier 316 and the current load cycle. Each loading cycle for the particular haulage work vehicle 10 may also be associated with a table, such that each table is populated by the data manager module 302 over a loading cycle of the haulage work vehicle 10. Thus, in one example, based on the determination of the start of a new loading cycle, the data manager module 302 may create a new data structure, such as a table, and store each of the associated current cycle data 320 and current load density 322 within that data structure until the end of loading cycle notification 218 is received. It should be noted that the storage of the associated current cycle data 320 and current load density 322 in tabular format is merely exemplary, as the datastore 304 may comprise an object orientated database.

The computation module 306 receives as input the associated current cycle data 320. Based on the associated current cycle data 320, the computation module 306 calculates a density (p) of the current load based on the ratio of its mass (m) to volume (V), wherein p is the density in kilograms per Liter (kg/L), m is the mass in kilograms (kg) determined from the mass data signal 318 of the current load cycle and V is the volume from the volume data 214 for the current load cycle. The computation module 306 stores the calculated density as the current load density 322 in the datastore 304. Generally, the computation module 306 stores the current load density 322 with the associated current cycle data 320 such that the data associated with a particular haulage work vehicle 10 for a particular load cycle of the loading work vehicle 12 includes the mass data determined from the mass data signal 318, the volume data 214 received from the loading work vehicle 12 and the current load density 322 determined or calculated by the computation module 306, each of which is associated with the haulage identifier 316.

Based on the associated current cycle data 320, the computation module 306 retrieves last cycle data 324 from the datastore 304. The last cycle data 324 is the last or previously stored associated data for the current loading cycle of the haulage work vehicle 10, which includes the associated current cycle data 320 and the current load density 322 for the last stored load cycle. Stated another way, the last cycle data 324 is the determined mass data, the volume data 214 and the load density for a previous load cycle, which is associated with the haulage identifier 316 and retrieved from the datastore 304.

Based on the last cycle data 324 and the associated current cycle data 320, the computation module 306 determines incremental volume change data 326 and incremental density change data 328. In one example, the computation module 306 calculates the incremental volume change data 326 by subtracting the volume data 214 of the last cycle data 324 from the volume data 214 of the associated current cycle data 320. The computation module 306 sets the incremental volume change data 326 for the haulage communication control module 310. In one example, the computation module 306 calculates the incremental density change data 328 by subtracting the last current density data 322 of the last cycle data 324 from the current load density 322. The computation module 306 sets the incremental density change data 328 for the haulage communication control module 310. Optionally, the computation module 306 may store the incremental volume change data 326 and the incremental density change data 328 in the datastore 304.

Based on the received associated current cycle data 320, the computation module 306 also determines whether the volume data 214 in the associated current cycle data 320 is greater than a predefined threshold. In one example, the predefined threshold is a factory set value, such as a rated heap capacity for the haulage work vehicle 10. If the volume data 214 is greater than the predefined threshold, the computation module 306 outputs overload notification 330. In various embodiments, the overload notification 330 is output to the human-machine interface 46 of the haulage work vehicle 10; however, the overload notification 330 may also be set for the haulage communication control module 310 and output by the haulage communication control module 310 to the loader controller 144 and/or the remote system 62.

Alternatively, based on the received associated current cycle data 320, the computation module 306 determines whether the determined mass data from the mass data signal 318 in the associated current cycle data 320 is greater than a predefined threshold, such as a predefined mass threshold. In one example, the predefined mass threshold is a factory set value, such as a rated capacity for the haulage work vehicle 10. If the determined mass data from the mass data signal 318 is greater than the predefined threshold, the computation module 306 outputs the overload notification 330. In various embodiments, the overload notification 330 is output to the human-machine interface 46 of the haulage work vehicle 10; however, the overload notification 330 may also be set for the haulage communication control module 310 and output by the haulage communication control module 310 to the loader controller 144 and/or the remote system 62.

The haulage communication control module 310 receives as input the incremental volume change data 326 and the incremental density change data 328. Based on the incremental volume change data 326 and the incremental density change data 328, the haulage communication control module 310 generates incremental change data 332, which is output to the remote system 62. The incremental change data 332 comprises the incremental volume change data 326 and the incremental density change data 328 for the particular load cycle.

The haulage communication control module 310 also receives as input the end of loading cycle notification 218. Based on the end of loading cycle notification 218, the haulage communication control module 310 retrieves loading cycle data 334 from the datastore 304. The loading cycle data 334 comprises the associated cycle data and density data for each of the load cycles for the completed loading cycle. Stated another way, the loading cycle data 334 is the mass data determined from the mass data signal 318, the volume data 214 and the current load density 322 for each load cycle completed by the loading work vehicle 12 during the loading cycle of the haulage work vehicle 10. The haulage communication control module 310 outputs the retrieved loading cycle data 334 to the remote system 62.

In certain embodiments, based on the retrieved loading cycle data 334, the haulage communication control module 310 determines or calculates total load density 336. In this example, the haulage communication control module 310 computes the total load density 336 by summing each of the current load density 322 values retrieved in the loading cycle data 334. The haulage communication control module 310 outputs the total load density 336 to the remote system 62. It should be noted that in certain embodiments, the total load density 336 is computed by the remote control module 66 based on the receipt of the loading cycle data 334 from the haulage communication control module 310.

Figure 4:
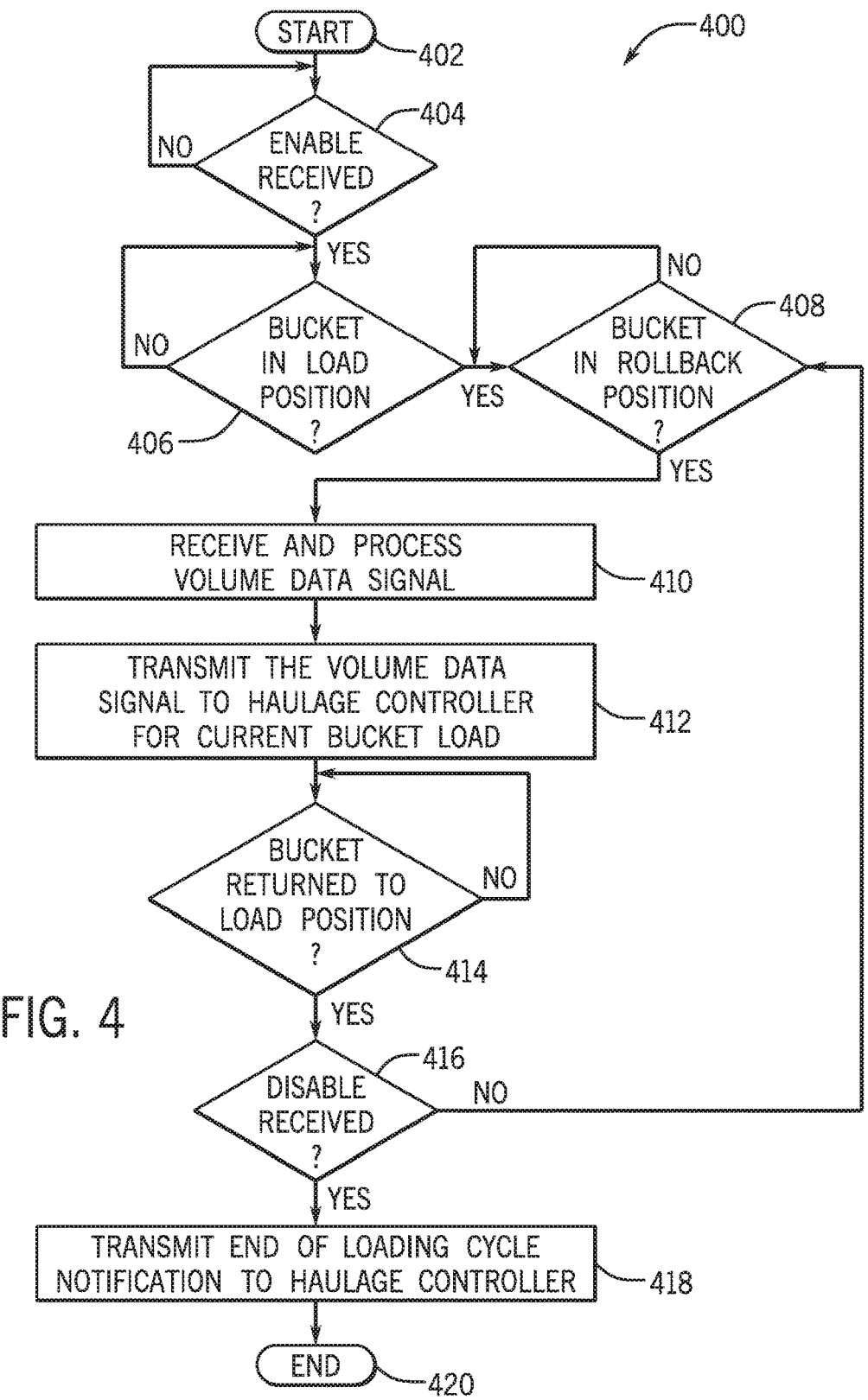
FIG. 4 is a flowchart illustrating an example control method of the disclosed load evaluation system performed by the loader evaluation system of FIG. 2 in accordance with various embodiments.

Referring now also to FIG. 4, a flowchart illustrates a control method 400 that may be performed by the loader controller 144 of FIGS. 1 and 2 in accordance with the present disclosure. As may be appreciated in light of the disclosure, the order of operation within the method is not limited to the sequential execution as illustrated in FIG. 4, but may be performed in one or more varying orders as applicable and in accordance with the present disclosure.

In various embodiments, the method may be scheduled to run based on predetermined events, and/or may run based on the receipt of the enable 206, for example.

In one example, with reference to FIG. 4, the method begins at 402. At 404, the method determines whether the enable 206 has been received. If true, the method proceeds to 406. Otherwise, the method loops.

At 406, the method determines, based on the bucket position data 210, whether the bucket 128 is in the load position L (FIG. 1A). If true, the method proceeds to 408. Otherwise, the method loops.

At 408, the method determines, based on the bucket position data 210, whether the bucket 128 is in the rollback position R (FIG. 1B). If true, the method proceeds to 410. Otherwise, the method loops.

At 410, the method receives and processes the volume data signal 212 from the sensor 152. In one example, the method processes the volume data signal 212 to determine whether the load bin 14 and/or the bucket 128 is in the image data received from the sensor 152. In this example, if true, the method transmits the processed volume data signal 212 as the volume data 214 to the haulage controller 44. The volume data 214 comprises the volume of material in the load bin 14 and/or the bucket 128 for the current load cycle as observed by the sensor 152.

At 414, the method determines, based on the bucket position data 210, whether the bucket 128 has returned to the load position L (FIG. 1A), such that the materials in the bucket 128 have been dumped into the load bin 14 (FIG. 1). If true, the method proceeds to 416. Otherwise, the method loops.

At 416, the method determines whether the disable 208 has been received. If true, the method proceeds to 418. Otherwise, the method loops to 408.

At 418, the method transmits the end of loading cycle notification 218 to the haulage controller 44. The method ends at 420.

Figure 5:
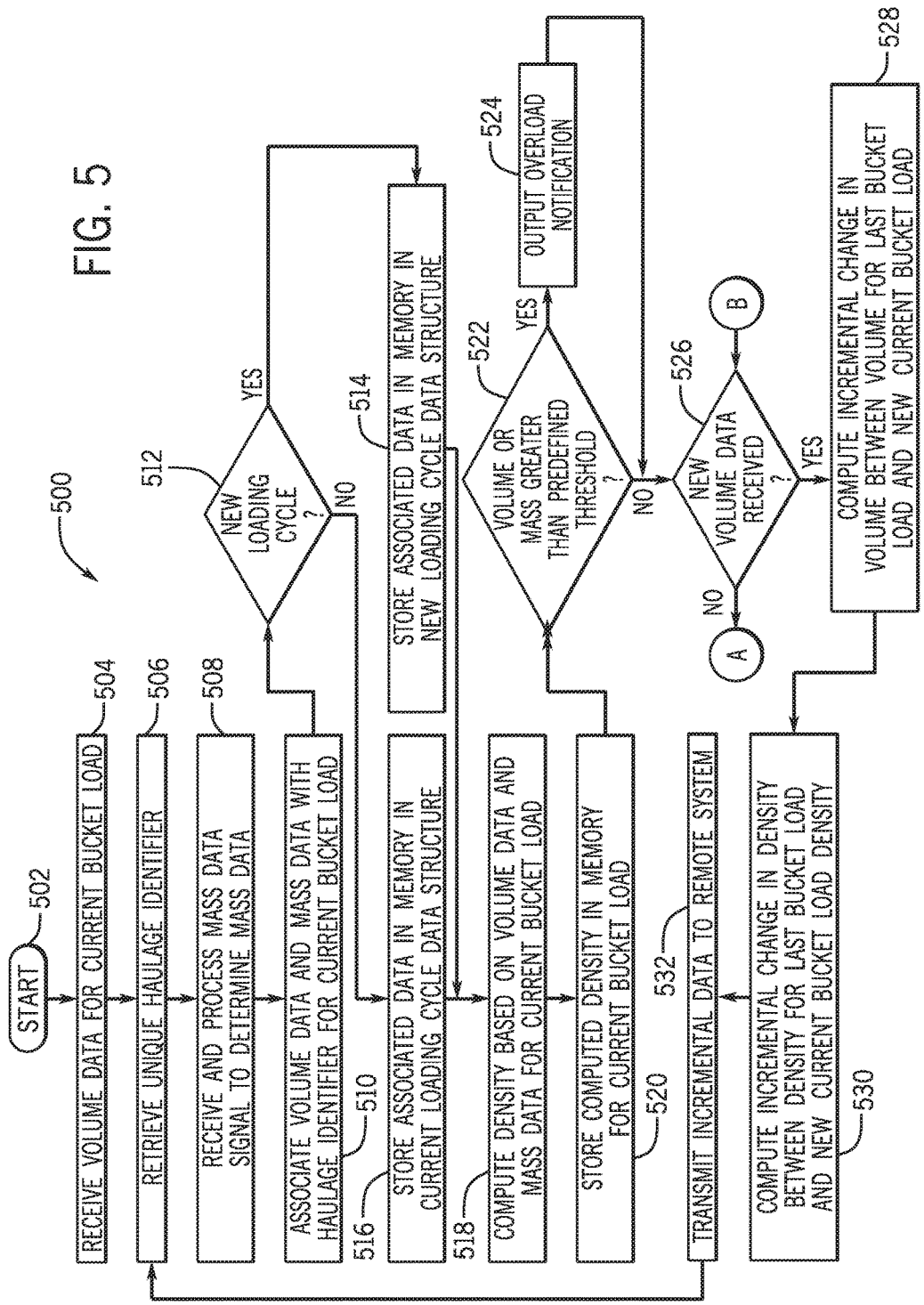
FIG. 5 is a flowchart illustrating an example control method of the disclosed load evaluation system performed by the haulage evaluation system of FIG. 3 in accordance with various embodiments.
Figure 6:
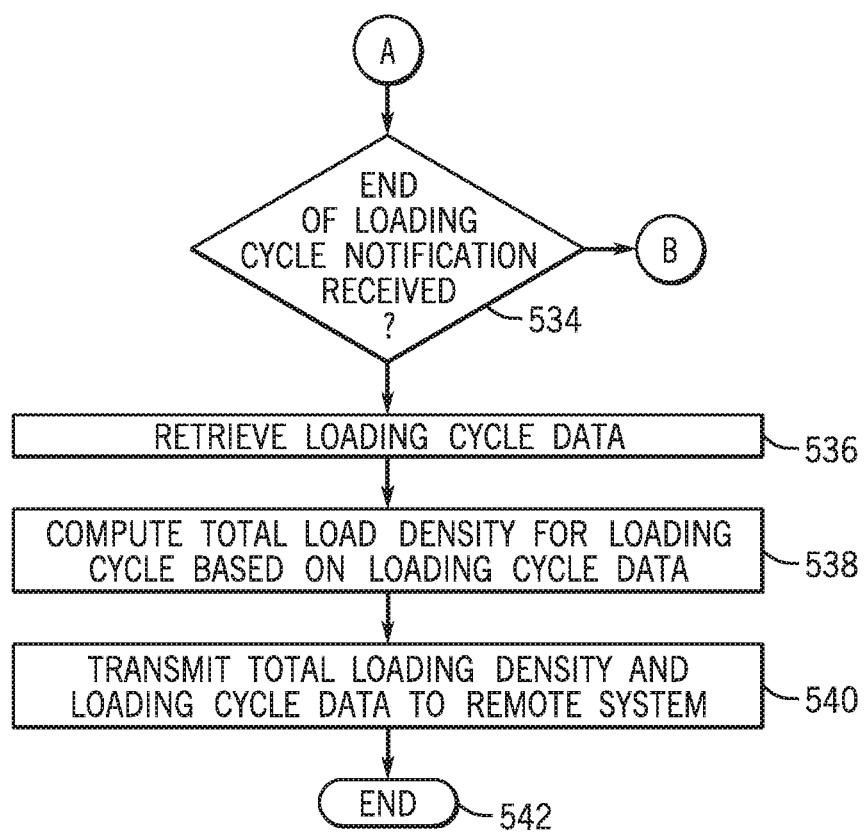
FIG. 6 is a continuation of the flowchart of FIG. 5 in accordance with various embodiments.

Referring now also to FIGS. 5 and 6, a flowchart illustrates a control method 500 that may be performed by the haulage controller 44 of FIGS. 1 and 3 in accordance with the present disclosure. As may be appreciated in light of the disclosure, the order of operation within the method is not limited to the sequential execution as illustrated in FIGS. 5 and 6, but may be performed in one or more varying orders as applicable and in accordance with the present disclosure.

In various embodiments, the method may be scheduled to run based on predetermined events, and/or may run based on the receipt of the volume data 214 from the loader controller 144, for example.

With reference to FIG. 5, the method begins at 502. At 504, the method receives the volume data 214 for the current load in the bucket 128 from the loader controller 144. At 506, the method retrieves the haulage identifier 316 from the memory associated with the haulage load evaluation control module 44a. At 508, the method receives and processes the mass data signal 318 from the sensor 52, and determines the mass data associated with the load bin 14. At 510, the method associates the volume data 214 and the mass data determined from the mass data signal 318 with the haulage identifier 316 for the current load in the bucket 128, thereby generating the associated current cycle data 320.

At 510, the method determines whether the associated current cycle data 320 is for a new loading cycle of the haulage work vehicle 10 based on whether the last communication received from the loading work vehicle 12 was an end of loading cycle notification 218. If the last communication was an end of loading cycle notification 218, the method determines a new loading cycle of the haulage work vehicle 10 has commenced, and proceeds to 514. Otherwise, if the last communication was volume data 214, the method determines that the current load in the bucket 128 is part of the current loading cycle of the haulage work vehicle 10, and proceeds to 516.

At 514, the method stores the associated data (the volume data 214 and the mass data determined from the mass data signal 318 with the haulage identifier 316 for the current load in the bucket 128 or the associated current cycle data 320) in a new loading cycle data structure in the datastore 304. At 516, the method stores the associated data (the volume data 214 and the mass data determined from the mass data signal 318 with the haulage identifier 316 for the current load in the bucket 128 or the associated current cycle data 320) in the current loading cycle data structure in the datastore 304.

At 518, the method computes the current load density 322 based on the associated current cycle data 320 using a density computation equation ($\rho=m/V$). At 520, the method stores the computed current load density 322 with the associated current cycle data 320 in the datastore 304. At 522, the method determines whether the volume data 214 is greater than the predefined threshold, such as the rated heap capacity for the haulage work vehicle 10. Alternatively, the method determines whether the determined mass from the mass data signal 318 is greater than the predefined threshold, such as the predefined mass threshold. If true, at 524, the method outputs the overload notification 330.

Otherwise, at 526, the method determines whether a new volume data 214 is received from the loader controller 144. If false, the method proceeds to A on FIG. 6. If true, the method proceeds to 528.

At 528, the method computes the incremental change in volume (i.e. incremental volume change data 326) between the volume data 214 of the last cycle data 324 and the new volume data 214 received from the loader controller 144. At 530, the method computes the incremental change in density (i.e. incremental density change data 328) between the current load density 322 of the last cycle data 324 and the current load density 322 computed based on the new volume data 214. At 532, the method transmits or outputs the incremental change data 332 to the remote system 62. The method loops to 506.

With reference to FIG. 6, from A, at 534, the method determines whether the end of loading cycle notification 218 has been received. If true, the method proceeds to 536. Otherwise, the method proceeds back to B on FIG. 5.

At 536, the method retrieves the loading cycle data 334. At 538, the method computes the total load density 336, based on the current load density 322 values from the loading cycle data 334. At 540, the method transmits the total load density 336 and the loading cycle data 334 to the remote system 62. The method ends at 542.

As will be appreciated by one skilled in the art, certain aspects of the disclosed subject matter may be embodied as a method, system (e.g., a work vehicle control system included in a work vehicle), or computer program product. Accordingly, certain embodiments may be implemented entirely as hardware, entirely as software (including firmware, resident software, micro-code, etc.) or as a combination of software and hardware (and other) aspects. Furthermore, certain embodiments may take the form of a computer program product on a computer-usable storage medium having computer-usable program code embodied in the medium.

Any suitable computer usable or computer readable medium may be utilized. The computer usable medium may be a computer readable signal medium or a computer readable storage medium. A computer-usable, or computer-readable, storage medium (including a storage device associated with a computing device or client electronic device) may be, for example, but is not limited to, an electronic, magnetic, optical, electromagnetic, infrared, or semiconductor system, apparatus, or device, or any suitable combination of the foregoing. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device. In the context of this document, a computer-usable, or computer-readable, storage medium may be any tangible medium that may contain, or store a program for use by or in connection with the instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be non-transitory and may be any computer readable medium that is not a computer readable storage medium and that may communicate, propagate, or transport a program for use by or in connection with an instruction execution system, apparatus, or device.

Aspects of certain embodiments are described herein may be described with reference to flowchart illustrations and/or block diagrams of methods, apparatus (systems) and computer program products according to embodiments of the invention. It will be understood that each block of any such flowchart illustrations and/or block diagrams, and combinations of blocks in such flowchart illustrations and/or block diagrams, may be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer-readable memory that may direct a computer or other programmable data processing apparatus to function in a particular manner, such that the instructions stored in the computer-readable memory produce an article of manufacture including instructions which implement the function/act specified in the flowchart and/or block diagram block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the flowchart and/or block diagram block or blocks.

Any flowchart and block diagrams in the figures, or similar discussion above, may illustrate the architecture, functionality, and operation of possible implementations of systems, methods and computer program products according to various embodiments of the present disclosure. In this regard, each block in the flowchart or block diagrams may represent a module, segment, or portion of code, which comprises one or more executable instructions for implementing the specified logical function(s). It should also be noted that, in some alternative implementations, the functions noted in the block (or otherwise described herein) may occur out of the order noted in the figures. For example, two blocks shown in succession (or two operations described in succession) may, in fact, be executed substantially concurrently, or the blocks (or operations) may sometimes be executed in the reverse order, depending upon the functionality involved. It will also be noted that each block of any block diagram and/or flowchart illustration, and combinations of blocks in any block diagrams and/or flowchart illustrations, may be implemented by special purpose hardware-based systems that perform the specified functions or acts, or combinations of special purpose hardware and computer instructions.

The terminology used herein is for the purpose of describing particular embodiments only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The description of the present disclosure has been presented for purposes of illustration and description, but is not intended to be exhaustive or limited to the disclosure in the form disclosed. Many modifications and variations will be apparent to those of ordinary skill in the art without departing from the scope and spirit of the disclosure. Explicitly referenced embodiments herein were chosen and described in order to best explain the principles of the disclosure and their practical application, and to enable others of ordinary skill in the art to understand the disclosure and recognize many alternatives, modifications, and variations on the described example(s). Accordingly, various embodiments and implementations other than those explicitly described are within the scope of the following claims.

What is claimed is:

1. A load evaluation system for assessing the loading of material from a loading work vehicle having a load bucket to a haulage work vehicle having a load bin, the load evaluation system comprising:
    at least one volume sensor including an imaging device or a detection and ranging device coupled to the loading work vehicle and configured to sense a volume of material in at least one of the load bucket and the load bin and generate a corresponding volume data signal; and
    a first controller onboard the loading work vehicle and a second controller onboard the haulage work vehicle, wherein at least one of the first and second controllers is configured to:
        receive the volume data signal from the at least one volume sensor;
        receive a unique haulage work vehicle identifier;
        associate volume data of the corresponding volume data signal with the unique haulage work vehicle identifier; and
        store in memory the associated volume data and haulage work vehicle identifier.

2. The load evaluation system of claim 1, wherein the first controller receives the volume data signal from the volume sensor and transmits the volume data signal to the second controller, and the second controller receives the unique haulage work vehicle identifier from memory and associates the volume data of the corresponding volume data signal with the unique haulage work vehicle identifier.

3. The load evaluation system of claim 2, wherein the second controller transmits the associated volume data and haulage work vehicle identifier to a remote processing system remote from the loading work vehicle and the haulage work vehicle.

4. The load evaluation system of claim 1, wherein the volume sensor generates a plurality of volume data signals having respective volume data for each of a plurality of bucket load cycles; and
    wherein at least one of the first and second controllers receives the plurality of volume data signals and for each bucket load cycle:
    associates the volume data of the corresponding volume data signal with the haulage work vehicle identifier; and
    stores in memory the volume data of the corresponding volume data signal for the associated haulage work vehicle.

5. The load evaluation system of claim 4, wherein at least one of the first and second controllers computes an incremental change in volume in the load bin based on a difference between volume data values stored in memory for consecutive bucket load cycles.

6. The load evaluation system of claim 4, further comprising:
    at least one mass sensor including a pressure sensor or an accelerometer coupled to the haulage work vehicle and configured to sense a mass of material in the load bin and generate a corresponding mass data signal.

7. The load evaluation system of claim 6, wherein at least one of the second controller and a remote processing system remote from the loading work vehicle and the haulage work vehicle receives the mass data signal; and
    wherein at least one of the second controller and the remote processing system compute a density based on mass data corresponding to the mass data signal and the volume data corresponding to the volume data signals.

8. The load evaluation system of claim 7, wherein the mass sensor generates a plurality of mass data signals having mass data for each of the plurality of bucket load cycles; and
    wherein at least one of the second controller and the remote processing system receives the plurality of mass data signals from the mass sensor and for each bucket load cycle:
    associates the mass data of the corresponding mass data signal with the stored volume data for the corresponding bucket load cycle; and
    stores in memory the mass data of the corresponding mass data signal.

9. The load evaluation system of claim 8, wherein at least one of the second controller and the remote processing system computes a density based on the associated mass data and volume data values for each bucket load cycle;
    wherein at least one of the second controller and the remote processing system stores the computed density value for each corresponding bucket load cycle; and
    wherein at least one of the second controller and the remote processing system computes an incremental change in density in the load bin based on a difference between density values stored in memory for consecutive bucket load cycles.

10. The load evaluation system of claim 9, wherein at least one of the second controller and the remote processing system compute a total load density value based on the stored density values.

11. The load evaluation system of claim 1, wherein at least one of the first controller, the second controller and a remote processing system remote from the loading work vehicle and the haulage work vehicle receives the volume data signal from the volume sensor and a mass data signal from a mass sensor coupled to the haulage work vehicle and computes a density based on volume data corresponding to the volume data signal and mass data corresponding to the mass data signal.

12. The load evaluation system of claim 1, wherein the loading work vehicle includes a boom and an arm coupled to the load bucket, and the volume sensor is coupled to the arm to observe the volume of material in the bucket and generate image data based thereon.

13. The load evaluation system of claim 1, wherein the loading work vehicle includes a boom and an arm coupled to the load bucket, and the volume sensor is coupled to the arm to observe the volume of material in the load bin and generate image data based thereon.

14. A load evaluation method for assessing the loading of material from a loading work vehicle having a load bucket to a haulage work vehicle having a load bin, the method comprising:
  sensing a volume of material in at least one of the load bucket and the load bin with at least one volume sensor including an imaging device or a detection and ranging device and generating a corresponding volume data signal;
  receiving, by a first controller onboard the loading work vehicle, the volume data signal from the at least one volume sensor;
  transmitting, by the first controller, volume data corresponding to the volume data signal to a second controller onboard the haulage work vehicle;
  associating, by the second controller, the volume data of the corresponding volume data signal with a unique haulage work vehicle identifier; and
  storing in memory the associated volume data and haulage work vehicle identifier.

15. The method of claim 14, further comprising:
  transmitting, by the second controller, the associated volume data and haulage work vehicle identifier to a remote processing system remote from the loading work vehicle and the haulage work vehicle.

16. The method of claim 14, further comprising:
  sensing a mass of material in the load bin with at least one mass sensor including a pressure sensor or an accelerometer coupled to the haulage work vehicle and generating a corresponding mass data signal; and
  computing, by the second controller, a density based on mass data corresponding to the mass data signal and the volume data corresponding to the volume data signal.

17. The method of claim 16, further comprising:
  determining an overload condition of the haulage work vehicle based on the volume data or the mass data.

18. The method of claim 14, further comprising:
  generating a plurality of volume data signals having respective volume data for each of a plurality of bucket load cycles by the volume sensor;
  receiving, by the second controller, the plurality of volume data signals and for each bucket load cycle:
  associating the volume data of the corresponding volume data signal with the haulage work vehicle identifier; and
  storing in memory the volume data of the corresponding volume data signal for the associated haulage work vehicle.

19. The method of claim 18, further comprising:
  computing, by the second controller, an incremental change in volume in the load bin based on a difference between volume data values stored in memory for consecutive bucket load cycles.

20. The method of claim 14, wherein the loading work vehicle includes a boom and an arm coupled to the load bucket, and the volume sensor is an imaging device coupled to the arm to observe the volume of material in the bucket and generate image data based thereon.

* * * * *